United States Patent
Dagum

(10) Patent No.: US 9,538,948 B2
(45) Date of Patent: Jan. 10, 2017

(54) METHOD AND SYSTEM FOR ASSESSMENT OF COGNITIVE FUNCTION BASED ON MOBILE DEVICE USAGE

(71) Applicant: Mindstrong, LLC, Los Altos Hills, GA (US)

(72) Inventor: Paul Dagum, Los Altos Hills, CA (US)

(73) Assignee: Mindstrong, LLC, Los Altos Hills, CA (US)

( * ) Notice: Subject to any disclaimer, the term of this patent is extended or adjusted under 35 U.S.C. 154(b) by 0 days.

(21) Appl. No.: 15/214,130

(22) Filed: Jul. 19, 2016

(65) Prior Publication Data

US 2016/0324457 A1    Nov. 10, 2016

Related U.S. Application Data

(63) Continuation of application No. 14/059,682, filed on Oct. 22, 2013, now Pat. No. 9,420,970.

(51) Int. Cl.
*A61B 5/16* (2006.01)
*A61B 5/00* (2006.01)
(Continued)

(52) U.S. Cl.
CPC ............ *A61B 5/16* (2013.01); *A61B 5/0022* (2013.01); *A61B 5/01* (2013.01); *A61B 5/021* (2013.01); *A61B 5/0476* (2013.01); *A61B 5/1112* (2013.01); *A61B 5/1118* (2013.01); *A61B 5/1123* (2013.01); *A61B 5/14532* (2013.01); *A61B 5/14551* (2013.01); *A61B 5/4815* (2013.01); *A61B 5/4866* (2013.01);
(Continued)

(58) Field of Classification Search
None
See application file for complete search history.

(56) References Cited

U.S. PATENT DOCUMENTS 7,837,472 B1 * 11/2010 Elsmore ............. G06F 19/3487
434/236
8,527,213 B2    9/2013 Kailas
(Continued)

OTHER PUBLICATIONS

Mirowski et al., Classification of Patterns of EEG Synchronization of Seizure Prediction, 2009.
(Continued)

*Primary Examiner* — Stanley K Hill
*Assistant Examiner* — Mikayla Chubb
(74) *Attorney, Agent, or Firm* — King & Spalding LLP

(57) ABSTRACT

A system and method that enables a person to unobtrusively assess their cognitive function from mobile device usage. The method records on the mobile device the occurrence and timing of user events comprising the opening and closing of applications resident on the device, the characters inputted, touch-screen gestures made, and voice inputs used on those applications, performs the step of learning a function mapping from the mobile device recordings to measurements of cognitive function that uses a loss function to determine relevant features in the recording, identifies a set of optimal weights that produce a minimum of the loss function, creates a function mapping using the optimal weights, and performs the step of applying the learned function mapping to a new recording on the mobile device to compute new cognitive function values.

17 Claims, 16 Drawing Sheets

(51) Int. Cl.
*A61B 5/11* (2006.01)
*A61B 5/01* (2006.01)
*A61B 5/1455* (2006.01)
*A61B 5/021* (2006.01)
*A61B 5/0476* (2006.01)
*A61B 5/145* (2006.01)
*G09B 5/12* (2006.01)
*G06F 19/00* (2011.01)
*G06N 5/02* (2006.01)

(52) U.S. Cl.
CPC .......... *A61B 5/4872* (2013.01); *A61B 5/6898* (2013.01); *A61B 5/7267* (2013.01); *A61B 5/749* (2013.01); *G06F 19/345* (2013.01); *G06N 5/022* (2013.01); *G09B 5/125* (2013.01); *A61B 2562/0219* (2013.01)

(56) References Cited

U.S. PATENT DOCUMENTS

| | | |
|---|---|---|
| 2003/0130595 A1 | 7/2003 | Mault |
| 2008/0229408 A1 | 9/2008 | Dinges |
| 2008/0242952 A1 | 10/2008 | Jung |
| 2009/0192417 A1* | 7/2009 | Mon-Williams ..... A61B 5/1124 600/595 |
| 2012/0059785 A1 | 3/2012 | Pascual et al. |
| 2013/0128060 A1 | 5/2013 | Rhoads et al. |
| 2013/0144537 A1 | 6/2013 | Schalk et al. |
| 2013/0179472 A1 | 7/2013 | Junqua |
| 2013/0254329 A1 | 9/2013 | Lin et al. |
| 2014/0075464 A1 | 3/2014 | McCrea |
| 2014/0081100 A1 | 3/2014 | Muhsin |
| 2014/0121559 A1 | 5/2014 | Stevens |
| 2014/0172467 A1 | 6/2014 | He |
| 2014/0249447 A1* | 9/2014 | Sereno ................. A61B 5/6898 600/558 |
| 2016/0100788 A1* | 4/2016 | Sano .................... A61B 5/6898 600/595 |

OTHER PUBLICATIONS

Wu et al., Multiscale Casual Connectivity Analysis by Canonical Correlation: Theory and Application to Epileptic Brain, 2011.
International Search Report and Written Opinion for PCT/US14/52227 dated Nov. 25, 2014.
International Search Report and Written Opinion for PCT/US14/52222 dated Dec. 2, 2014.

* cited by examiner

901

| session_id | key_type | key_code | key_desc | key_press_time | key_release_time | key_press_duration |
|---|---|---|---|---|---|---|
| 1381345092707 | 1 | 104 | h | 2013-10-09 11:58:17.524 | 2013-10-09 11:58:17.686 | 162 |
| 1381345092707 | 1 | 101 | e | 2013-10-09 11:58:18.319 | 2013-10-09 11:58:18.497 | 178 |
| 1381345092707 | 1 | 108 | l | 2013-10-09 11:58:19.241 | 2013-10-09 11:58:19.504 | 263 |
| 1381345092707 | 1 | 108 | l | 2013-10-09 11:58:20.133 | 2013-10-09 11:58:20.265 | 132 |
| 1381345092707 | 1 | 111 | o | 2013-10-09 11:58:20.572 | 2013-10-09 11:58:20.720 | 148 |
| 1381345092707 | 2 | 32 | SPACE | 2013-10-09 11:58:21.351 | 2013-10-09 11:58:21.356 | 5 |
| 1381345092707 | 1 | 119 | w | 2013-10-09 11:58:21.992 | 2013-10-09 11:58:22.181 | 189 |
| 1381345092707 | 1 | 111 | o | 2013-10-09 11:58:22.477 | 2013-10-09 11:58:22.642 | 165 |
| 1381345092707 | 1 | 114 | r | 2013-10-09 11:58:23.46 | 2013-10-09 11:58:23.219 | 173 |
| 1381345092707 | 1 | 108 | l | 2013-10-09 11:58:23.727 | 2013-10-09 11:58:23.866 | 139 |
| 1381345092707 | 1 | 100 | d | 2013-10-09 11:58:24.268 | 2013-10-09 11:58:24.429 | 161 |
| 1381345092707 | 2 | 32 | SPACE | 2013-10-09 11:58:25.220 | 2013-10-09 11:58:25.222 | 2 |
| 1381345092707 | 2 | 10 | ENTER | 2013-10-09 11:58:27.1 | 2013-10-09 11:58:27.139 | 138 |

Figure 9(a)

| app_pkg_name | view_name_in_pkg | scroll_unit | item_count | from_idx | to_idx | scroll_direction | max_scroll | scroll_value | timestamp |
|---|---|---|---|---|---|---|---|---|---|
| com.android.email | android.widget.ListView | 1 | 30 | 2 | 10 | 0 | 0 | 0 | 10/9/2013 19:06 |
| com.android.email | android.widget.ListView | 1 | 30 | 4 | 12 | 0 | 0 | 0 | 10/9/2013 19:06 |
| com.android.email | android.widget.ListView | 1 | 30 | 7 | 15 | 0 | 0 | 0 | 10/9/2013 19:06 |
| com.android.email | android.widget.ListView | 1 | 30 | 8 | 16 | 0 | 0 | 0 | 10/9/2013 19:06 |
| com.android.email | android.widget.ListView | 1 | 30 | 11 | 18 | 0 | 0 | 0 | 10/9/2013 19:06 |
| com.android.email | android.widget.ListView | 1 | 30 | 13 | 20 | 0 | 0 | 0 | 10/9/2013 19:06 |
| com.android.email | android.widget.ListView | 1 | 30 | 14 | 21 | 0 | 0 | 0 | 10/9/2013 19:06 |
| com.android.email | android.widget.ListView | 1 | 30 | 15 | 23 | 0 | 0 | 0 | 10/9/2013 19:06 |
| com.android.email | android.widget.ListView | 1 | 30 | 17 | 24 | 0 | 0 | 0 | 10/9/2013 19:06 |
| com.android.email | android.widget.ListView | 1 | 30 | 18 | 26 | 0 | 0 | 0 | 10/9/2013 19:06 |
| com.android.email | android.widget.ListView | 1 | 30 | 19 | 27 | 0 | 0 | 0 | 10/9/2013 19:06 |
| com.android.email | android.widget.ListView | 1 | 30 | 21 | 28 | 0 | 0 | 0 | 10/9/2013 19:06 |
| com.android.email | android.widget.ListView | 1 | 30 | 21 | 29 | 0 | 0 | 0 | 10/9/2013 19:06 |

| lattitude | longitude | altitude | bearing | speed (m/s) | accuracy | timestamp |
|---|---|---|---|---|---|---|
| 37.69942816 | -122.4719009 | 69 | 176.6000061 | 28.57008934 | 19 | 10/9/2013 17:07 |
| 37.62496588 | -122.4288145 | 58 | 149.5 | 34.5 | 16 | 10/9/2013 17:12 |
| 37.55374861 | -122.3782415 | 36 | 150.8000031 | 31.25399971 | 30 | 10/9/2013 17:17 |
| 37.43185458 | -122.2394988 | 230 | 135.6999969 | 32.5 | 38 | 10/9/2013 17:27 |
| 37.3892418 | -122.1629877 | 255 | 112.6999969 | 5.5 | 53 | 10/9/2013 17:32 |
| 37.37288021 | -122.1447374 | 216 | 143.3000031 | 4.123105526 | 34 | 10/9/2013 17:37 |
| 37.36548784 | -122.1159025 | 172 | 61.90000153 | 6.519202232 | 33 | 10/9/2013 17:42 |

Figure 9(c)

METHOD AND SYSTEM FOR ASSESSMENT OF COGNITIVE FUNCTION BASED ON MOBILE DEVICE USAGE

RELATED APPLICATION

The present application is a continuation application of and claims priority to U.S. patent application Ser. No. 14/059,682, filed Oct. 22, 2013, and titled "Method and System for Assessment of Cognitive Function Based on Mobile Device Usage". The foregoing application is hereby incorporated herein by reference in its entirety.

BACKGROUND

Field of Art

The invention relates generally to computing a person's cognitive function and, more specifically, to unobtrusive assessment of cognitive function from mobile device usage.

Background Art

An aging society and increasing lifespan has resulted in an increased prevalence of cognitive decline in society from mild cognitive impairment to Alzheimer's disease. Today, one in eight older Americans has Alzheimer's disease and Alzheimer's is the sixth leading cause of death in the United States [1]. By 2025, the number of Americans age 65 and older with Alzheimer's disease is estimated to increase 30% and by 2050 that number is expected to triple, barring any breakthroughs to prevent, slow or arrest the disease [1]. Prior to developing Alzheimer's disease, patients go through a six-year prodromal phase of cognitive decline. The societal burden of mental disease in the elderly is staggering and poised to worsen.

Repeat studies have demonstrated that a healthy lifestyle of moderate physical activity, good diet, and social interaction can preserve cognitive function and reverse cognitive decline [2,3,4]. Several of these studies use group comparisons between intervention and control groups and rely on tests of cognitive function pre-intervention and post-intervention to assess the intervention effects on cognitive function [5,6]. But for most individuals, knowing that healthy habits preserve cognitive function is not sufficiently motivating until it is too late and the damage is well underway. By the time a family member or physician first discovers signs of cognitive impairment the subject has suffered substantial atrophy and loss of key structural brain regions necessary for memory, learning, executive function, and attention. Neuropsychological tests administered by a neurologist show high specificity for cognitive impairment but low sensitivity.

The emergence of online tests available through many application vendors such as BrainBaseline [7] may help detect signs of impairment earlier but only if the subject is highly motivated and persistent in testing themselves repeatedly and regularly for years. Highly motivated individuals are more likely to have healthy habits including physical activity, diet, and social interaction and least likely to benefit from close surveillance of online behavioral tests, further limiting the value of those tests to the broader segment of society that would benefit most. In addition, test practice effects are well documented [8,9] whereby the subject develops test taking skills that increase their scores but do not transfer well to real world activities and further undermine the test's sensitivity and specificity to cognitive decline.

The introduction of mobile devices and their broad adoption has revolutionized how society interacts both with each other and with their surroundings. A smartphone today enables a user to make calls, send and receive emails and text messages, find their location on a map or retrieve directions to a destination point, browse the internet, download and play game applications, and a host of other activities. In addition, these smartphones are equipped with accelerometers and gyroscopes that sense the device's acceleration and orientation in 3-dimensions. Processing of the acceleration and orientation signals reveals the user's activity such as whether the person is walking or jogging.

One company that has leveraged the close interaction of an individual with their mobile device to make behavioral assessments is Ginger.io [10,11]. Ginger.io provides a smartphone application that tracks the number and frequency of calls, text messages, and emails sent, and uses the device's global positioning system (GPS) and accelerometer to infer activity level. The target population for Ginger.io's application is patients with chronic diseases such as diabetes, mental disease, and Chron's disease. When a patient deviates from their routine calling and texting patterns, Ginger.io alerts the individual's caregiver to intervene and assess the situation for noncompliance with medications, inappropriate titration of medications, and other factors that may precipitate a flare-up of the patient's disease.

In Ginger.io's application, changes in routine calling, texting, or location are interpreted as symptoms of disease flare-up requiring investigation and notably have high false positives rates. Cognitive decline due to aging is an insidious process over several years where subtle declines in physical activity, diet changes, and social engagement are causal, not symptomatic. Diagnosing cognitive decline requires frequent assessment of the higher order cognitive processes of executive function, working memory, episodic memory, and attention.

What is needed is a method and system to assess cognitive function that is highly sensitive, specific, and unobtrusive to an individual.

1. Alzheimer's Association, 2012 Alzheimer's Disease Facts and Figures. www.alz.org/downloads/facts_figures_2012.pdf
2. Christopher Hertzog, et al., Enrichment Effects on Adult Cognitive Development: Can the Functional Capacity of Older Adults Be Preserved and Enhanced? *Association for Psychological Science*, 2009, 9(1):1-65
3. Interview with Nicholas Spitzer, Crosswords don't make you clever. *The Economist*, August, 2013, http://www.economist.com/blogs/prospero/2013/08/quick-study-neuroscience
4. Gretchen Reynolds, How exercise can help us learn. *New York Times*, August 2013, http://well.blogs.nytimes.com/2013/08/07/how-exercise-can-help-us-learn/?_r=0
5. Interview with J. Carson Smith, Exercise may be the best medicine for Alzheimer's disease. *Science Daily*, July 2013, http://www.sciencedaily.com/releases/2013/07/130730123249.htm
6. J. Carson Smith, et al., Interactive effects of physical activity and APOE-e4 on BOLD semantic memory activation in healthy elders. *Neuroimage*, January 2011; 54(1):635-644
7. www.brainbaseline.com
8. Ackerman P L, Individual differences in skill learning: An integration of psychometric and information processing perspectives. *Psychol Bull*, 1987, 102:3-27
9. Healy A F, Wohldmann E L, Sutton E M, Bourne L E, Jr, Specificity effects in training and transfer of speeded responses. *J Exp Psychol Learn Mem Cognit*, 2006, 32:534-546

10. www.ginger.io
11. Owen Covington, 'Virtual nurse' helps Forsyth Medical Center track diabetics. *The Business Journal*, May 2013, http://www.bizjournals.com/triad/news/2013/05/20/forsyth-medical-center-using-virtual.html

BRIEF SUMMARY OF INVENTION

The invention enables a person to monitor changes in their cognitive function in an unobtrusive manner, to view those changes over time, and to evaluate the impact that changes in their social engagement, physical activity, learning activity, and diet have on their cognitive function evaluation. What is needed is a method and system to assess cognitive function that is highly sensitive, specific, and unobtrusive to an individual. Such a method and system would measure and track a person's cognitive function without explicit input or behavioral changes required by the subject, such as repeated neuropsychological evaluations and online tests. Rather, the method and system would use digitally recorded interactions of an individual with their mobile devices to compute assessments of cognitive function, detect changes in cognitive function, and infer attribution to changes in behavioral activity without disrupting the user's day-to-day activities or their use of mobile devices.

One embodiment of the present invention is a method for unobtrusively recording an individual's interaction with their mobile device including applications opened, inputs typed, gesture patterns used on a touch-screen, and voice input. The method of the present invention can include the step of recording data from the mobile device's global positioning system (GPS), accelerometer, and gyroscope to infer daily activity including the activity intensity, daily mobility including method of travel, and daily social engagement through latitude and longitude localization of travel destination to a shopping center, a museum, or a restaurant. This data will provide insight regarding an individual lifestyle, including their social skills, level of activity and dietary habits. These items can contribute to good health and/or they can be indicative of a problem. The method of the present invention can further include the step of recording data from the mobile device's phone, email, and texting applications to capture incoming and outgoing calls, emails and texts generated, length of conversation, length of messages, and discrepancies in voice messages and email messages opened versus received, which are used as additional inputs to infer changes in social engagement.

The method of the present invention can further include the step of recording data from a barcode scanning application used to scan purchased grocery items, food and beverages consumed, and supplementing that data with nutritional fact information to track diet attributes such as caloric input, calories from fat, consumed saturated fats, trans fats, cholesterol, sugars, protein, vitamins and minerals. This information is also indicative of lifestyle that is healthy or not. This information can also correlate to an increase or decline in an individual's cognitive function. The method of the present invention can further include the step of recording data from wearable devices that measure, by way of example, heart-rate, blood oxymetry, body temperature, electroencephalogram, and communicate that information to an application resident on the mobile device to infer the user's physical activity, activity intensity, and learning activity. This information related to an individual's biological vitals can explain why there is a change in cognitive function and why the change is not problematic and/or this information can be an indicator of a systemic problem that will have a long term negative impact on cognitive function. The method can further include the step of recording the URLs visited on an Internet browser application, e-book pages read on an e-book application resident on the mobile device, the content classification of the material read and its level of complexity, and the language of the content, to further infer learning activity by the user.

The data captured from the user's mobile device by the method of the present invention is persisted in the device's storage and further transmitted to a cloud computing system to compute cognitive function from the user's interactions and to infer behavioral activity attribution effects on changes in cognitive function. The cognitive function assessment and behavioral activity attributions are presented to the user in a password protected online portal that reveals positive and negative contributors to trends in cognitive function assessment and establishes behavioral targets to improve cognitive function. Those targets, and any ensuing improvement or decline in cognitive function are subsequently measured by the method of the present invention, enabling an unobtrusive, closed-loop method and system for assessing and improving cognitive function from mobile device usage. The cloud computing environment allows a user to change mobile devices and/or mobile device service carriers and still have access to previously recorded data.

The system and method as claimed enables a person to unobtrusively assess their cognitive function from mobile device usage. The method records on the mobile device the occurrence and timing of user events comprising the opening and closing of applications resident on the device, the characters inputted, touch-screen gestures made, and voice inputs used on those applications, performs the step of learning a function mapping from the mobile device recordings to measurements of cognitive function that uses a loss function to determine relevant features in the recording, identifies a set of optimal weights that produce a minimum of the loss function, creates a function mapping using the optimal weights, and performs the step of applying the learned function mapping to a new recording on the mobile device to compute new cognitive function values.

The system and method as claimed enables a person to unobtrusively quantify the effect of mobility, physical activity, learning, social interaction and diet on cognitive function. The method records on the mobile device one of global positioning system longitude and latitude coordinates, accelerometer coordinates, and gyroscope coordinates, one of outgoing and incoming phone calls, outgoing and incoming emails, and outgoing and incoming text messages, one of URLs visited on an internet browser application, books read on an e-reader application, games played on game applications, and the nutritional content of food consumed, performs the step of learning a function mapping from those recordings to measurements of cognitive function using a loss function to identify a set of optimal weights that produce a minimum for the loss function, uses those optimal weights to create the function mapping, and performs the step of computing the variance of the cognitive function measurements that is explained by the function mapping to assign an attribution to the effect of mobility, physical activity, learning, social interaction, and diet on measured changes in cognitive function.

These and other advantageous features of the present invention will be in part apparent and in part pointed out herein below.

BRIEF DESCRIPTION OF THE DRAWING

For a better understanding of the present invention, reference may be made to the accompanying drawings in which:

FIG. 9(*a*)-(*c*) is representative of data encoded unobtrusively by the in vivo monitoring module in accordance with one embodiment of the present invention.

Figure 1:
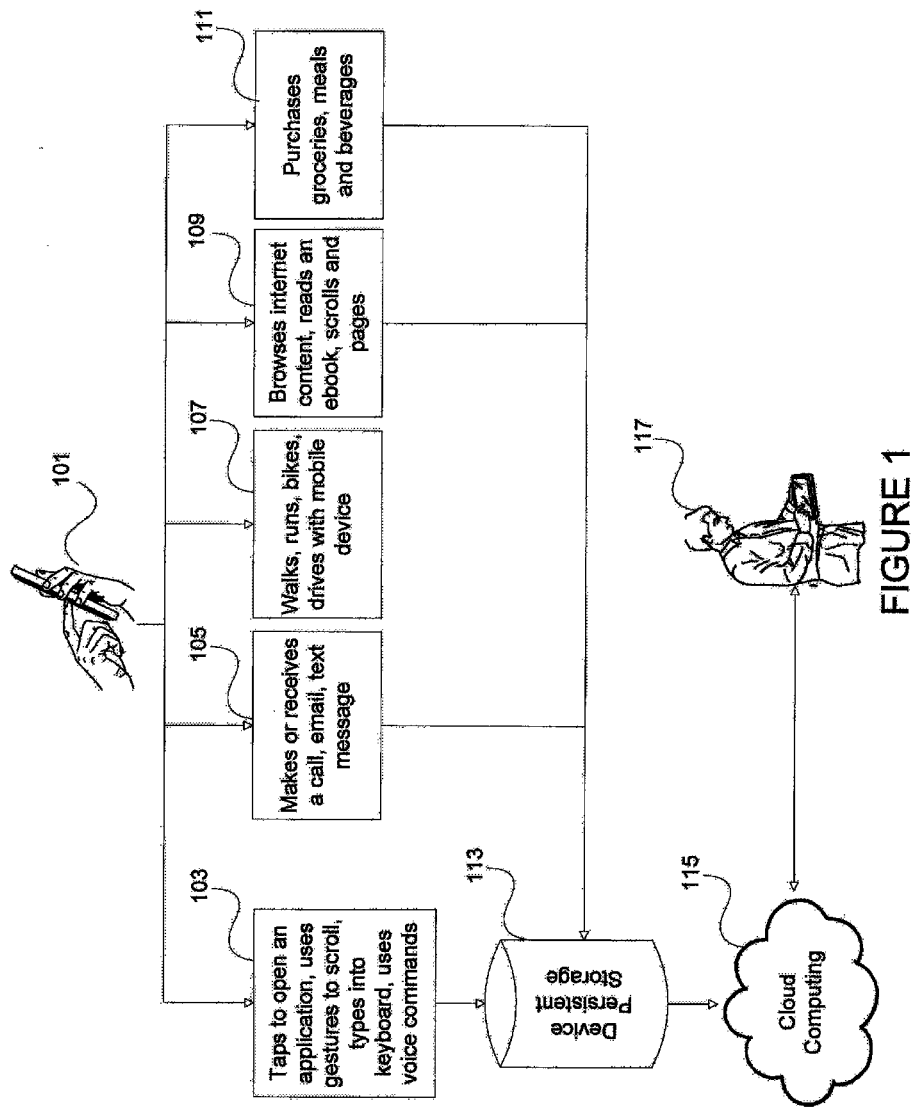
FIG. 1 illustrates an embodiment of the unobtrusive cognitive function assessment system configured in accordance with the present invention.

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DETAILED DESCRIPTION

According to the embodiment(s) of the present invention, various views are illustrated in FIG. 1-8 and like reference numerals are being used consistently throughout to refer to like and corresponding parts of the invention for all of the various views and figures of the drawing.

The following detailed description of the invention contains many specifics for the purpose of illustration. Any one of ordinary skill in the art will appreciate that many variations and alterations to the following details are within scope of the invention. Accordingly, the following implementations of the invention are set forth without any loss of generality to, and without imposing limitations upon, the claimed invention.

One implementation of the present invention comprises a system and method that enables an unobtrusive assessment of a person's cognitive function from mobile device usage, which embodiment teaches a novel system and method for recording on the mobile device the occurrence and timing of user events comprising the opening and closing of applications resident on the device, the characters inputted and the touch-screen gestures used on those applications, the embodiment further includes performing the step of learning a function mapping from the mobile device recordings to measurements of cognitive function that uses a loss function to determine relevant features in the recording, identifies a set of optimal weights that produce a minimum of the loss function, creates a function mapping using the optimal weights, the embodiment further includes performing the step of applying the learned function mapping to a new recording on the mobile device to compute a new cognitive function value. For example, a mixed model function is a type of function containing both fixed and random effects and is used in settings where repeated measurements are made over time on the same subjects. The mixed model function can be utilized for the learned function mapping, which develops the appropriate attribution for the cognitive function from the repeated measurements. For the cognitive function a deep belief network, a machine learning function composed of layers of neural networks capable of learning complex high-level features, can be utilized. A software application can reside on a mobile computing device, such as a smart phone, personal data assistant (PDA), or tablet computer such that when it is executed by the processor of the computing device, the steps of the method are performed.

Another implementation of the present invention comprises a system and method that enables a person to unobtrusively quantify the effect of physical activity on cognitive function, which embodiment teaches a novel system and method for repeatedly recording on the mobile device one of global positioning system longitude and latitude coordinates, accelerometer coordinates, and gyroscope coordinates, the implementation further includes performing the step of learning a function mapping from those recordings to measurements of cognitive function using a loss function to identify a set of optimal weights that produce a minimum for the loss function, uses those optimal weights to create the function mapping, the embodiment further includes performing the step of computing the variance of the cognitive function measurements that is explained by the function mapping to assign an attribution to the effect of physical activity on measured changes in cognitive function.

A further implementation of the present invention comprises a system and method that enables a person to unobtrusively quantify the effect of social activity on cognitive function, which embodiment teaches a novel system and method for repeatedly recording on the mobile device one of outgoing and incoming phone calls, outgoing and incoming emails, and outgoing and incoming text messages, the implementation further includes performing the step of learning a function mapping from those recordings to measurements of cognitive function using a loss function to identify a set of optimal weights that produce a minimum for the loss function, uses those optimal weights to create the function mapping, the embodiment further includes performing the step of computing the variance of the cognitive function measurements that is explained by the function mapping to assign an attribution to the effect of social activity on measured changes in cognitive function.

A further implementation of the present invention comprises a system and method that enables a person to unobtrusively quantify the effect of learning activity on cognitive function, which embodiment teaches a novel system and method for repeatedly recording on the mobile device one of URLs visited on an Internet browser application, books read on an e-reader application, games played on game applications, the implementation further includes performing the step of learning a function mapping from those recordings to measurements of cognitive function using a loss function to identify a set of optimal weights that produce a minimum for the loss function, uses those optimal weights to create the function mapping, the embodiment further includes performing the step of computing the variance of the cognitive function measurements that is explained by the function mapping to assign an attribution to the effect of learning activity on measured changes in cognitive function.

A further implementation of the present invention comprises a system and method that enables a person to unobtrusively quantify the effect of diet on cognitive function, which embodiment teaches a novel system and method for repeatedly recording on the mobile device the nutritional content of food consumed, the implementation further includes performing the step of learning a function mapping from those recordings to measurements of cognitive function using a loss function to identify a set of optimal weights that produce a minimum for the loss function, uses those optimal weights to create the function mapping, the embodiment further includes performing the step of computing the variance of the cognitive function measurements that is explained by the function mapping to assign an attribution to the effect of diet on measured changes in cognitive function.

The loss function for the cognitive function can evaluate baseline recordings and changes and trends in the recordings both from a quantitative and qualitative perspective. For example the frequency of events can be monitored for cognitive measurement as well as the quality of each event, such as latencies between gestures or keystrokes, erroneous keystrokes or gestures, duration of key presses, misspellings and other activity.

Another implementation of the invention can be a computer system comprising a mobile computer (for example a smart-phone; tablet or PDA computing device) including a wireless network interface which communicates over a wireless network with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, wherein the mobile computer system includes various executable program modules stored thereon where when executed are operable to perform functions.

The computer system can comprise an in vivo monitoring module stored on a mobile computer where when executed records to the memory unit of said mobile computer the occurrence and timing of user events comprising the opening and closing of applications resident on said mobile computer, the characters inputted in said applications, and the touch-screen gestures made on said applications. The type of the event and both the frequency and timing of the events and the various qualitative metrics regarding the event is recorded. A transmission module can also be stored on said mobile computer where when executed transmits through the wireless network interface the recordings stored in the memory unit to said second computer. A cognitive function module can be stored on said second computer where when executed learns a function mapping from said transmitted recording to measurements of cognitive function using a loss function to determine relevant features (including frequency, timing and qualitative metrics) in said recording, identifies a set of optimal weights that produce a minimum for said loss function, and creates said function mapping using said optimal weights. A plan module can also be stored on said second computer where when executed applies said function mapping to a new transmitted recording of the occurrence and timing of events comprising the opening and closing of applications resident on said device, the characters inputted in said applications, and the touch-screen gestures made on said applications, to calculate a new cognitive function value.

Another implementation of the invention can be a computer system comprising a mobile computer including a wireless network interface which communicates with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, wherein the mobile computer system includes various executable program modules stored thereon where when executed are operable to perform functions.

The computer system can comprise a motion module stored on said mobile computer where when executed records to the memory unit of said mobile computer one of global positioning system longitude and latitude coordinates, accelerometer coordinates, and gyroscope coordinates. In another implementation, the computer system can comprise a social module stored on said mobile computer where when executed records to the memory unit of said mobile computer one of outgoing and incoming phone calls, outgoing and incoming emails, and outgoing and incoming text messages. In another implementation, the computer system can comprise a learning module stored on said mobile computer where when executed records to the memory unit of said mobile computer one of URLs visited on an internet browser application, books read on an e-reader application, games played on game applications. In another implementation, the computer system can comprise a diet module stored on said mobile computer where when executed records nutritional content of food consumed.

In any of the preceding implementations, a transmission module can be stored on said mobile computer where when executed transmits through the wireless network interface the recordings stored in the memory unit to said second computer. In any of the preceding implementations, an attribution module can be stored on said second computer where when executed learns a function mapping from said transmitted recording to measurements of cognitive function using a loss function to identify a set of optimal weights that produce a minimum for said loss function, and creates said function mapping using said optimal weights. In any of the preceding implementations, a plan module can be stored on said second computer where when executed presents to the user the attribution to said cognitive function measurements that are explained by said recordings.

The details of the invention and various embodiments can be better understood by referring to the figures of the drawing. FIG. 1 illustrates an implementation of the functional description of the system configured in accordance with the present invention and is not intended to limit scope as one of ordinary skill would understand on review of this application that other configurations could be utilized without departing from the scope of the claimed invention. Referring to FIG. 1 an individual uses his or her mobile device 101. In 103, the individual taps the touch-screen to open an application, uses touch-screen gestures to scroll within an application, types messages, directions, and other content on a keyboard exposed by the application or uses voice commands to do the same, reads and scrolls through content, and makes calls or listens to messages. The user's activity in 103 is recorded on the device's persistent storage 113. In 105, the user makes or receives calls, email messages, and text messages.

The date and time of that activity, the activity duration, and the sender and recipient phone number or email address are recorded in the device's persistent storage 113. The frequency of each event is recorded and the various qualitative characteristics of each event are also recorded. In 107, the user carries the mobile device with them while driving, using public transportation, walking, biking or running. While engaging in these activities, the mobile device's global positioning system (GPS) records the user's longitude and latitude coordinates in 107. Similarly, in 107, the device's acceleration and gyroscopic motion along a 3-coordinate system is recorded. The type of locations to which the individual traveled can be determined and the characteristic of the motion of the user can also be evaluated for fluidity or erratic motion. This information is recorded in the device's persistent storage 113. In 109, the user browses URLs on an Internet browser application resident on the mobile device, or reads an e-book on an e-book reader resident on the mobile device. The URLs browsed and the pages of the e-book read, the start time and end time between URLs and pages are recorded by 109 and persisted in 113.

Note that all gesture activity, typing activity, and voice command activity during the use of applications tracked in 105, 107, and 109 is captured separately in 103 and recorded with the time and application in which that activity took place. In this way, the system tracks gestures used during browsing, paging and scrolling, for example. Lastly, in 111 a bar code scanning application resident on the mobile device enables the user to scan grocery purchases, and meals and beverages purchased when the latter have bar codes. The bar code scanning application has access to a database of nutritional facts. If the nutritional fact for the scanned bar code is not in the database, then in 111 the application instructs the user to photograph the nutritional fact label of the item. The bar code information and any photographs are persisted in 113.

The data captured in the device's persistent storage 113 is transmitted to cloud computers 115. Transmission uses a secure channel and can use hypertext transfer protocol secure (HTTPS) to securely transfer the data to 115. The cloud computers 115 analyze the recorded data against historical recordings and against recordings averaged over other users demographically matched to the existing user. The output of the analysis is an evaluation of cognitive function and the attribution to changes in behavioral activities inferred from the activities recorded in 105-111 including social engagement 105, physical activity 107, learning activity 109, and diet 111. The user in 117 logs into his or her personal password protected online account to view the results of the analysis in 115 together with suggestions for improvement.

In one implementation of the method and system, in order to establish a baseline of data, supervised benchmark testing can be conducted on an initial test group of individuals where these individuals take a neuropsychological benchmark test for cognitive function and the data is stored. Each of the same individuals who are tested can be provided with mobile devices having the computer program for performing the system and method. Data for each individual can be recorded as outlined herein and the data from the mobile device usage can be correlated to the benchmark testing results and cognitive function. Cognitive function levels and bands can also be determined from the result. Once certain baselines have been established and correlations are made between cognitive function and mobile device usage, all subsequent mobile device usage by individuals can be utilized to improve the system and method as learning occurs. The learning from the subsequent mobile device usage can be considered unsupervised learning.

Figure 2:
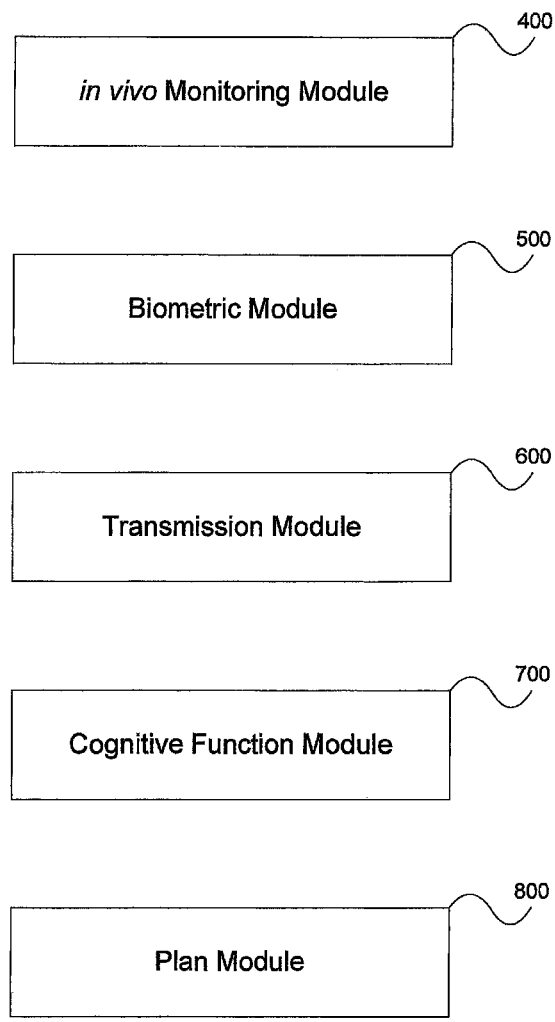
FIG. 2 is a functional description of the system in accordance with one embodiment of the present invention.

FIG. 2 illustrates an implementation of the functional description of the system configured in accordance with the present invention and is not intended to limit scope as one of ordinary skill would understand on review of this application that other configurations could be utilized without departing from the scope of the claimed invention. Referring to FIG. 2, a user's interaction with a mobile device is captured and recorded by the in vivo monitoring module 400. The biometric module 500 confirms that the user's interactions captured by the in vivo monitoring module 400 truly correspond to the mobile device owner and appropriately marks the recordings made by that module. The transmission module 600 is responsible for transmitting the recorded data to a cloud computer within 24-hours of the recording and more regularly when possible using broadband WiFi for the transmission or other transmission means including 4G LTE transmission provide by subscriber data plans. This module is also responsible for securing an encrypted channel before transmitting the recorded data.

The cognitive function module 700 extracts base features and higher-order features from the data, learns a predictive model of cognitive function, and makes cognitive function assessments of the user from new inputs recorded by the in vivo monitoring module 400. Module 700 also computes the attribution of the user's behavioral activities inferred from recordings made by module 400 to the user's cognitive function assessments. The plan module 800 provides an online login account for the user and designated individuals to review current and historical cognitive function trends, behavior activity attribution to those trends, how well the user is tracking to target behavior activity and target cognitive function, and further enables the user to update those targets.

Figure 3:
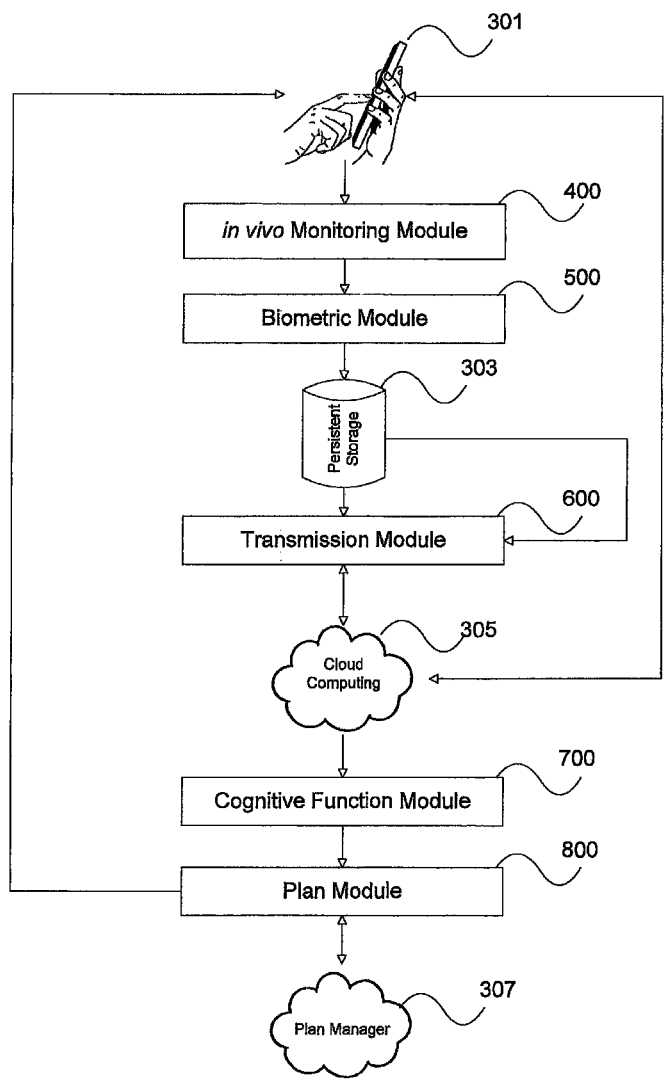
FIG. 3 illustrates an exemplary computing environment of the unobtrusive cognitive function assessment system configured in accordance with one embodiment of the present invention.

FIG. 3 illustrates an implementation of the computing environment of the system configured in accordance with the present invention and is not intended to limit scope as one of ordinary skill would understand on review of this application that other configurations could be utilized without departing from the scope of the claimed invention. Referring to FIG. 3, a user downloads and installs a software application to their mobile device 301 from a computer in the cloud 305. The software application comprises the in vivo monitoring module 400, the biometric module 500, and the transmission module 600. These three modules read and write to the mobile device's persistent storage 303. The in vivo monitoring module 400 writes raw activity data to the persistent storage 303. The biometric module 500 detects the new activity data and computes a biometric signature from the data. If the biometric signature does not match the user's biometric signature computed from historical data, the module requests the user to enter identifying credentials into a pop-up displayed on the mobile device. If the user fails to confirm their identity, or cancels, the recorded data is marked as "non-user" generated data.

The transmission module 600 transmits the data persisted in storage 303 with the annotation of the data as user or non-user generated that is computed by module 500 to the cloud computers 305. The cognitive function module 700 resides in the cloud computers 305 and computes a cognitive function value from the user's mobile device usage and further computes the attribution of behavioral activity, inferred from mobile device usage, to cognitive function value changes. The module then compares the user's cognitive function value and inferred behavioral activity to the behavioral norm of the user's prior data, and against plan targets set by the plan manager 307 in the plan module 800. The results of the cognitive function module 700 are recorded in the plan module 800 also residing in the cloud computers 305 and are made available for review by the user and the plan manager 307. The plan manager 307 is appointed by the user and may include the user, members of the user's family, and healthcare providers.

Figure 4:
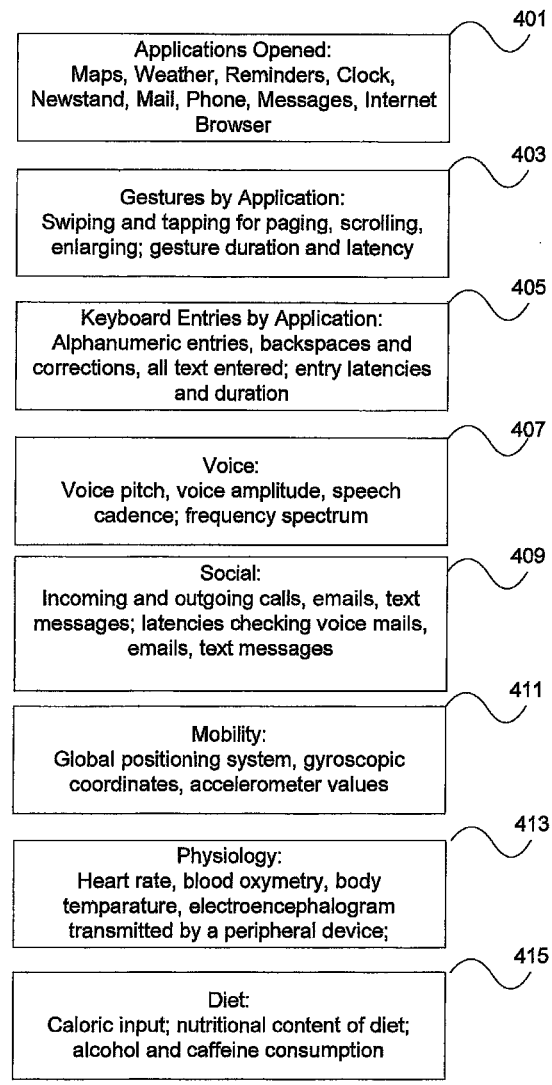
FIG. 4 is the in vivo monitoring module in accordance with one embodiment of the present invention.

FIG. 4 illustrates an embodiment of the in vivo monitoring module configured in accordance with the present invention and is not intended to limit scope as one of ordinary skill would understand on review of this application that other configurations could be utilized without departing from the scope of the claimed invention. Referring to FIG. 4, a mobile device such as smartphone, a tablet computer, and other similar devices can have many applications available to the user. These applications include, but are not limited to, maps used for directions and global positioning localization, weather, reminders, clock, newsstand configured with user selected publications, mail configured by the user to include personal and work email, phone configured by the user to include contacts, messages for texting, and an internet browser.

Module 401 tracks the application opened, the date-time that it was opened, the date-time that it was closed and records that information on the device's persistent storage. Upon opening an application, the user interacts with the application through keyboard inputs, voice, and gestures. In 403, applications running on devices that support touchscreen gestures are recorded. The gestures include swiping and tapping and 403 records the application, datetime, gesture type, gesture duration and latency between gestures. In 405, keyboard entries are recorded for applications enabling a keyboard. All keyboard entries are recorded, which includes alphanumeric entries, backspace entries, capitalization, formatting entries, and editing entries. Module 405 further records the latency and duration of each keyboard entry and other qualitative metrics. All recordings are stored in the device's persistent storage with the application name and date-time of the entry.

Module 407 records voice during phone conversations and during voice-input commands. The number called, or application receiving the voice command, and the date-time of the voice input are recorded together with the voice in the device's persistent storage. Module 409 records outgoing and incoming email, text messages, and calls and further records recipient and sender email address, recipient and sender text message phone number, and outgoing and incoming phone number. The information is stored in the device's persistent storage together with the date-time of the event.

For mobile devices equipped with a global positioning system (GPS), module 411 samples the device's location and time stamps the input. For mobile devices equipped with a gyroscope and an accelerometer, module 411 further samples the three gyroscopic coordinates and the three accelerometer coordinates. The GPS, gyroscope, and accelerometer samples are time stamped and recorded in the device's persistent storage.

Recordings from peripheral accessories that measure heart rate, blood pressure, blood glucose, oxymetry, body temperature, electroencephalograms, and transmit those measurements to an application resident on a mobile device are persisted in module 413. The data transmitted by those peripheral devices is time stamped. The peripheral accessories can be used to obtain biological vital signs of the individual, which can be used to determine if a decline in cognitive function data is due to a vital sign such as fatigue or low blood-glucose levels rather than an actual decline in cognitive function of the individual. The biological vitals can also be used as an alert of a biological trend that will have a long term negative impact on cognitive function, such as hypertension.

Module 415 enables a barcode scanning application enhanced with nutritional fact information appended to each barcode entry, that tracks and records caloric input, nutritional content, alcohol, and caffeine consumption. The dietary information can be used as an alert of a dietary trend that will have a long term negative impact on cognitive function, such as high alcohol intake or high fat or cholesterol intake.

Figure 5:
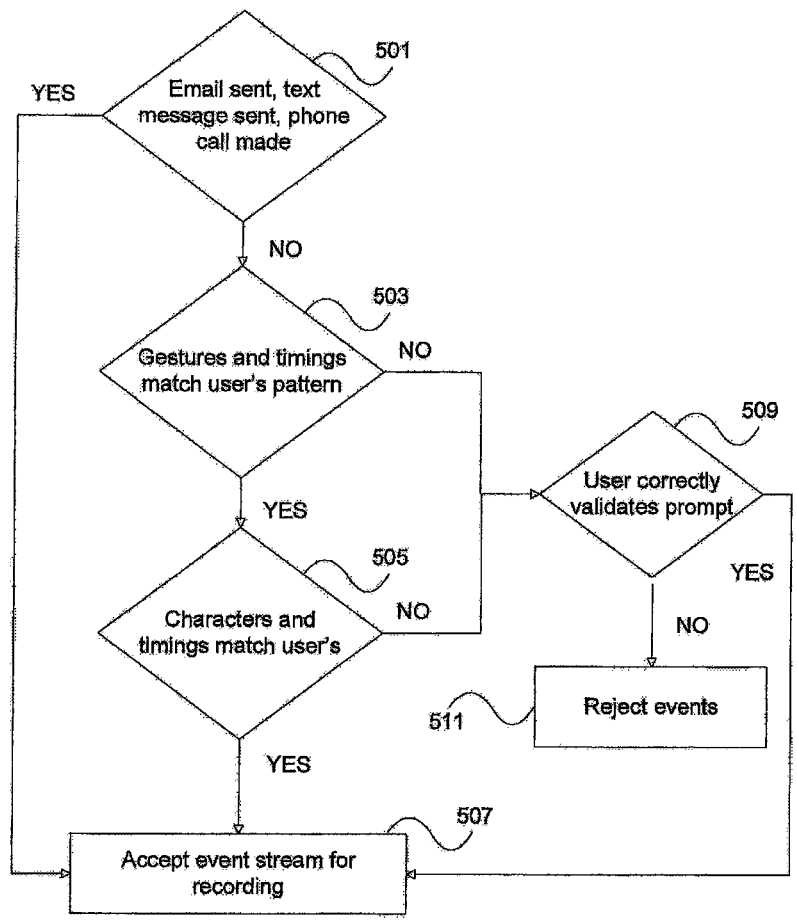
FIG. 5 is the biometric module in accordance with one embodiment of the present invention.

FIG. 5 illustrates an implementation of the biometric module configured in accordance with the present invention and is not intended to limit scope as one of ordinary skill would understand on review of this application that other configurations could be utilized without departing from the scope of the claimed invention. Referring to FIG. 5, the biometric module infers from the recorded activity on the mobile device whether the activity was initiated by the user or by someone else. As others may access the user's device for spurious reasons, correctly inferring true from false user activity is necessary.

In 501, sending an email from the mobile device, making a call from the mobile device, or sending a text message from the mobile device confirms user identity. 501 then passes control to 507, which accepts the event recordings as user-generated. If 501 does not detect said activity, then it passes control to 503 which evaluates the newly recorded gestures and gesture timings against a plurality of gesture signatures recorded for the user. If 503 establishes a signature match of the gestures, it passes control to 505 to further evaluate newly recorded character patterns and timings against a plurality of character signatures recorded for the user. If 505 establishes a signature match from the observed characters it passes control to 507 which accepts the events recorded as user-generated. If either 503 or 505 fail to establish a signature match, they pass control to 509 that prompts the user for validation. If the user validates correctly, 509 passes control to 507, and if not, control is transferred to 511 and the recorded events are rejected.

Figure 6:
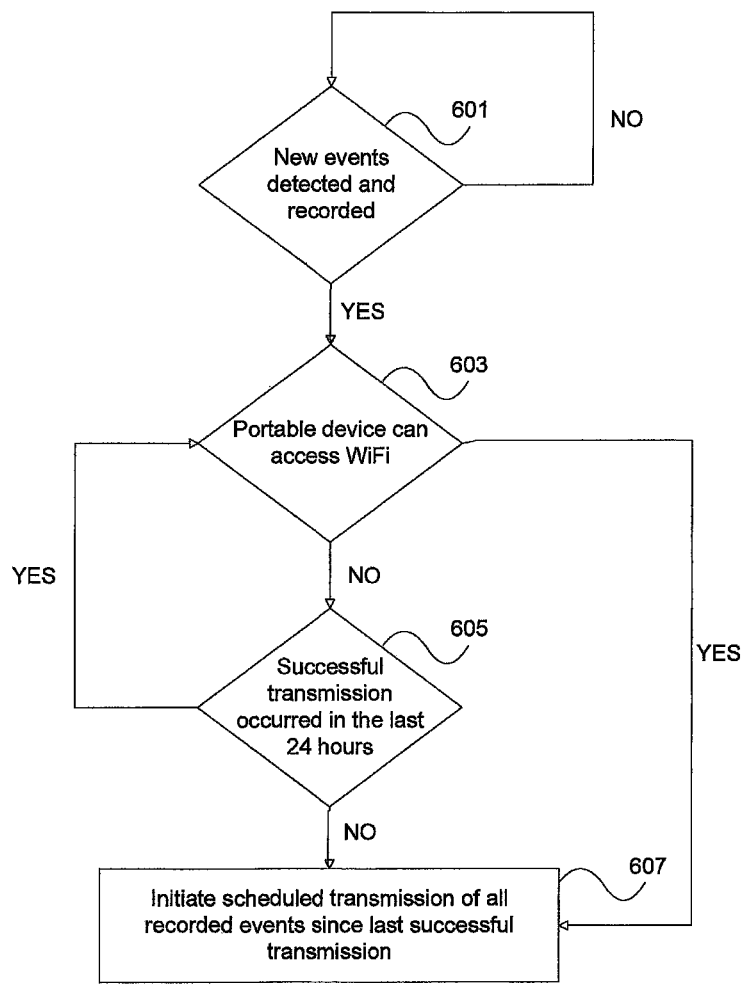
FIG. 6 is the transmission module in accordance with one embodiment of the present invention, FIG. 7(*a*)-(*d*) is the cognitive function module in accordance with one embodiment of the present invention, FIG. 8(*a*)-(*c*) is the plan module in accordance with one embodiment of the present invention.

FIG. 6 illustrates an implementation of the transmission module of the system configured in accordance with the present invention and is not intended to limit scope as one of ordinary skill would understand on review of this application that other configurations could be utilized without departing from the scope of the claimed invention. Referring to FIG. 6, the transmission module is a background process that runs on the mobile device and sleeps until it is awaken by the recording of new events on the device in 601. Upon recording new activity, 601 passes control to 603 that attempts to establish WiFi access. If 603 succeeds, then it passes control to 607 to initiate transmission of all recorded activity since the last successful transmission. If 603 fails then it passes control to 605 of the transmission module which evaluates whether a successful transmission occurred within a 24 hour period. If 605 determines that no successful transmission has occurred within a 24 hour period, it passes control to 607 to initiate transmission of all recorded activity since the last successful transmission. If, however, 605 confirms that a successful transmission has occurred within 24 hours, it returns control to 603.

Figure 7A:
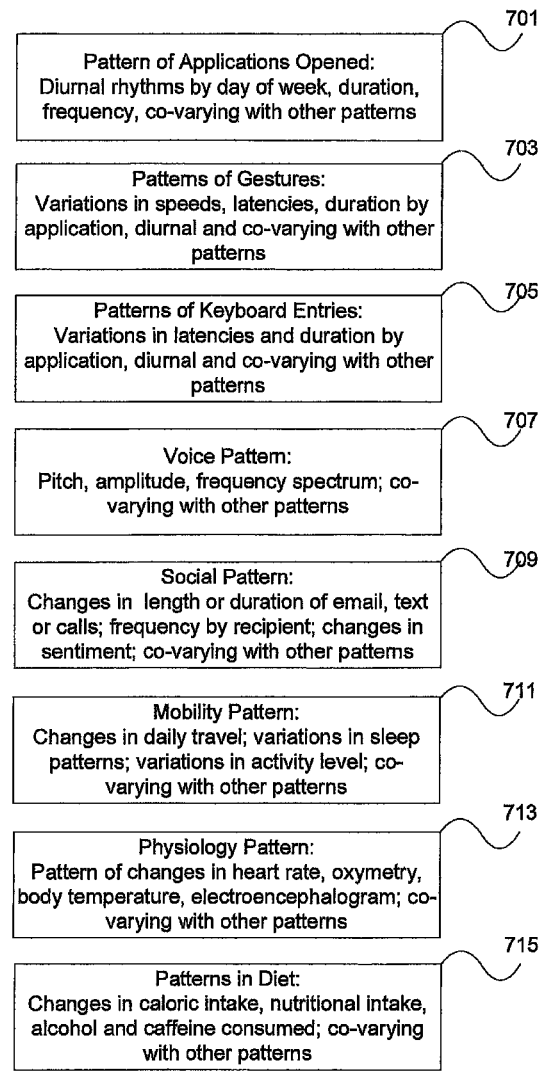

FIG. 7(a)-(d) illustrate an embodiment of the cognitive function module configured in accordance with the present invention and is not intended to limit scope as one of ordinary skill would understand on review of this application that other configurations could be utilized without departing from the scope of the claimed invention. Referring to FIG. 7(a), the cognitive function module accesses the recordings made by the in vivo monitoring module and transmitted to the cloud computers 305 of FIG. 3. Patterns in a user's interactions with a mobile device captured in 701-707 are analyzed for changes in cognitive function. In 701, changes in applications opened and closed by a user, frequency and latencies between opening and closing, and their diurnal and weekly variations are inputs to the feature extraction, learning, and computation of cognitive function illustrated in FIGS. 7(b) and 7(c). In 703, changes in a user's gestures on a touch-screen such as type of gesture, gesture durations, including false positive gestures of excessive scrolling during search and excessive paging during browsing, are additional inputs to the feature extraction, learning, and computation.

Similarly, in 705 character inputs, recurring spelling mistakes, omissions, excessive backspace corrections, irregular latency variances in common words, length of messages, and message coherence are inputs into the feature extraction, learning, and computation of cognitive function. Lastly, in 707 signal processing of speech and voice provides additional input to the computation including emerging irregularities in phones and phoneme latencies, and narrowing or shifting of the voice frequency spectrum. The time of day and day of week are captured in the recordings of 701-707 and used by the cognitive function computation to adjust, or explain variances that can be attributed to individual fatigue and other factors that have short-term effects on cognitive function.

Further, to correct for motion artifact such as from driving or walking, GPS, gyroscope and accelerometer recordings made in 411 are used as additional inputs in the feature extraction, learning and computation of cognitive function. Lastly, to correct for physiologic effects such as anxiety, general malaise, illness, the physiologic measurements of heart-rate, blood oxymetry, and body temperature when available and recorded in 413, are used as further inputs to the evaluation of cognitive function.

In 709-715, behavioral activities recorded on the mobile device are analyzed to explain changes in the cognitive function that is computed using inputs 701-707. In 709, a user's incoming and outgoing email, phone calls, and text messages, their frequencies and length are used as a proxy for the user's level of social engagement. In 711, a user's daily travel, the inferred mode of travel including vehicle, bicycle, foot or other, the user's sleep and rest patterns inferred by mobile device "quiet" times, are used to infer physical activity. In 713, when this data is available and when correlated with physical activity data in 711, rapid heart rates from anxiety or illness are distinguished from exercise induced changes, improving the inference of physical activity and quantifying the intensity of that activity. In 715, analysis of patterns in groceries purchased, food and drinks consumed provides a proxy to nutritional intake.

Figure 7B:
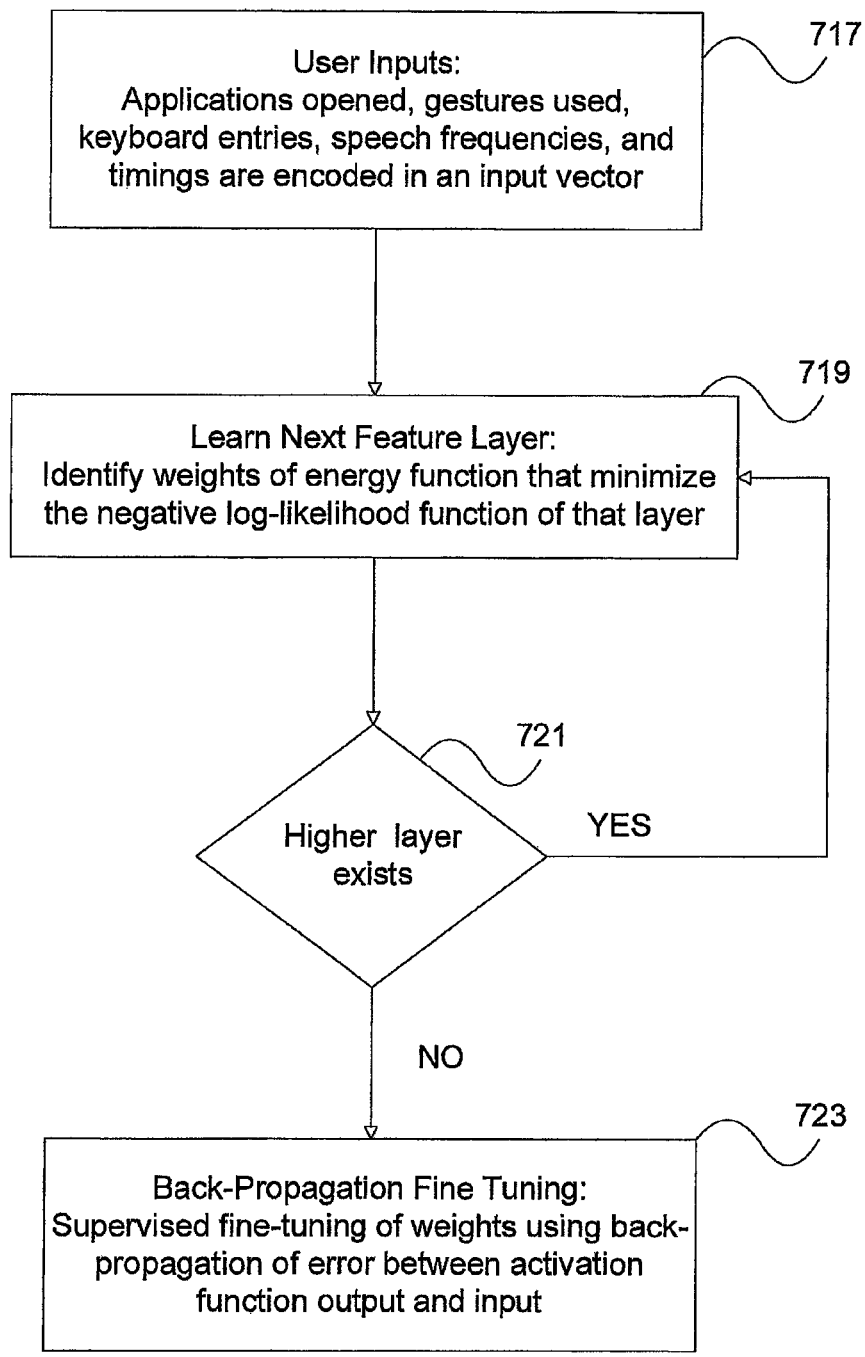
Figure 7C:
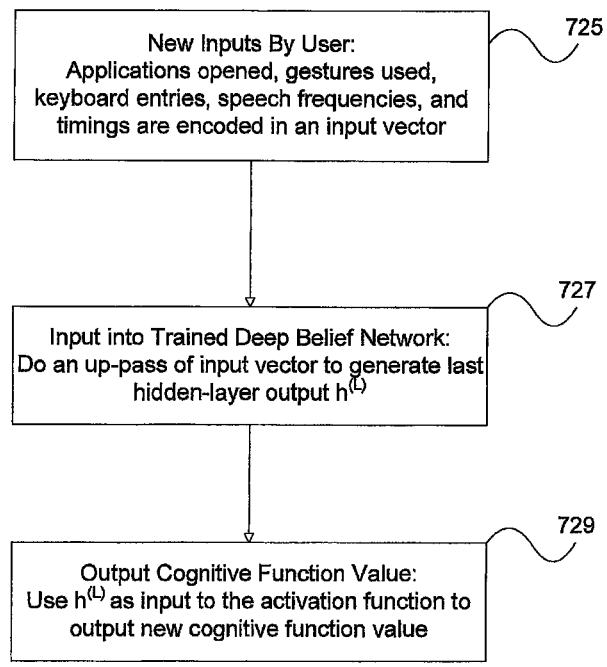

FIGS. 7(b) and 7(c) illustrate an implementation of the feature extraction, learning, and computation of cognitive function configured in accordance with the present invention, and is not intended to limit scope as one of ordinary skill would understand on review of this application that other configurations could be utilized without departing from the scope of the claimed invention. Referring to FIG. 7(b), mobile device recordings in 717 are encoded in the input vector of the visible layer of a deep belief network. The inputs in 717 comprise the mobile usage recorded in 401-405 and if available, further comprise voice recordings 407. In 719 the first layer of features is learned from a stochastic gradient search that minimizes the negative log-likelihood function of the input vector. In 721, if higher unlearned layers exist, control is passed back to 719 and another layer of higher-order features is learned using as input the values from the lower hidden layer. If no further layers exist, 721 passes control to 723, where the weights learned in 719 are fine-tuned using back-propagation of the errors between the output from an activation function applied to the last hidden layer with inputs 717 and the cognitive function measure associated with those inputs.

Referring to FIG. 7(c), once the cognitive function computational model is fully trained in 717-723, future recordings of device usage 725 is input into the visible layer of the cognitive function computational model 727. An up-propagation of the input generates the last hidden-layer output $h^{(L)}$ that is inputted into the activation function in 729 to generate a new cognitive function value.

Figure 7D:
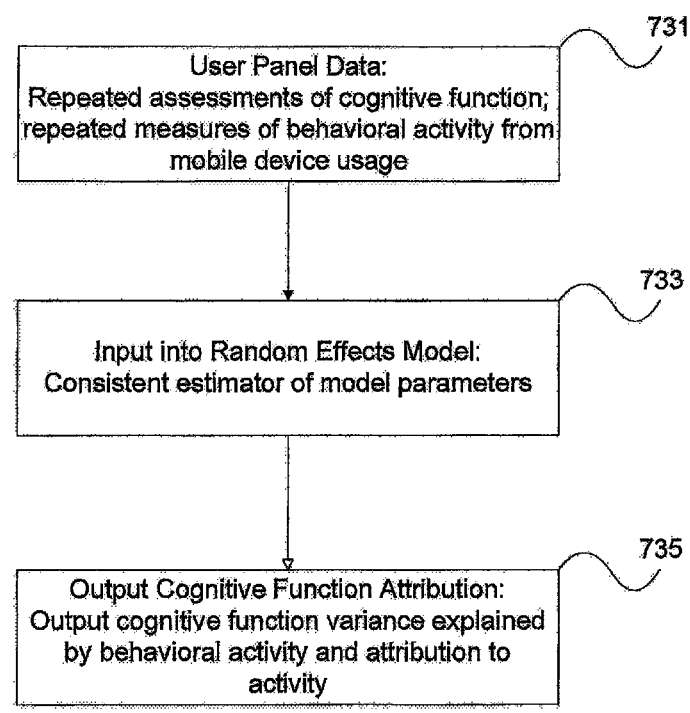

FIG. 7(d) illustrates an implementation of the attribution module configured in accordance with the present invention, and is not intended to limit scope as one of ordinary skill would understand on review of this application that other configurations could be utilized without departing from the scope of the claimed invention. Referring to FIG. 7(d), 731 stores the repeated evaluations of cognitive function illustrated in FIG. 7(c) and the recordings of each user's behavioral activity inferred from the mobile device illustrated in 709-715. In 733, consistent estimator of the parameters of a random effects regression is applied to the data in 731. The random effects regression with the parameters computed in 733 is used to compute the variance in cognitive function values that is explained by the behavioral data in 731. Further, 735 computes the attribution of the behavioral activities 409-415 to changes in cognitive function values stored in 731.

Figure 8A:
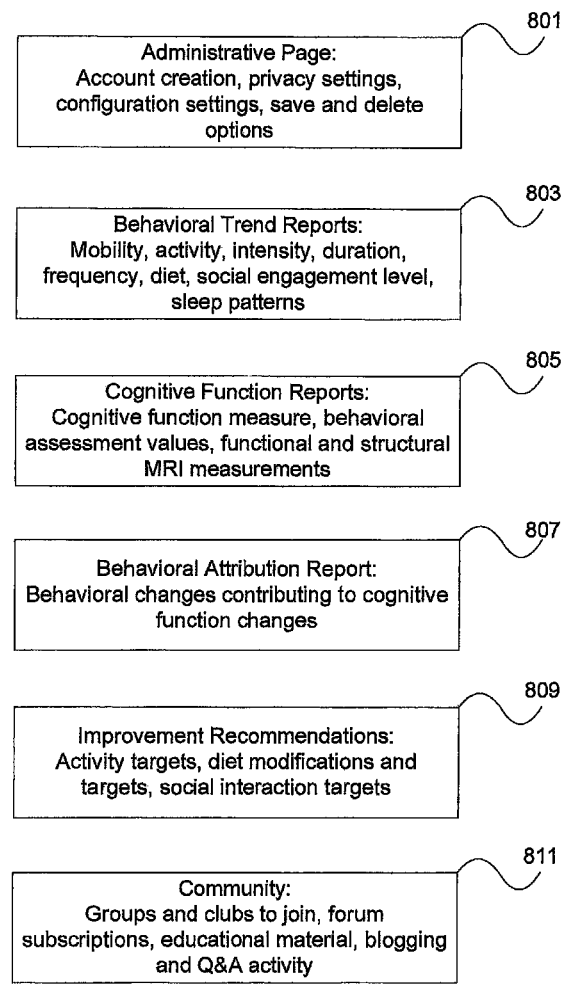

FIG. 8(a) illustrates an embodiment of the functional description of the plan module configured in accordance with the present invention and is not intended to limit scope as one of ordinary skill would understand on review of this application that other configurations could be utilized without departing from the scope of the claimed invention. Referring to FIG. 8(a), the user creates and accesses an online account to obtain aggregated and detailed views of recorded data, cognitive function evaluation and target recommendations to improve cognitive function. In 801, the user creates an account and inputs personal demographic data and health data. The user also sets privacy levels. In 803, the user accesses recent and historical views of aggregated recordings of (i) mobility, (ii) activity, (iii) social, (iv) learning, (v) diet, (vi) applications used, (vii) electroencephalogram (EEG), and (viii) physiology. A calendar widget enables the user to specify the aggregation period to use for the recent view and the historical views. Each group of recordings offers granular views of behavior. Activity reports on physical activity and intensity, social engagement reports on outbound and inbound number of distinct people called, emailed, or text messaged, learning engagement reports on URLs visited and ebooks read, subject type and language, diet reports on food and beverages consumed and nutritional facts, applications reports on type of application, application name, duration and frequency of use, EEG reports on electroencephalogram recordings, and physiology reports on heart rate, pulse oxymetry, and body temperature by time of day.

805 presents a time-series of the cognitive function evaluations computed in 725-729. If neuropsychological evaluations of cognitive function are available these are overlaid on the time-series in 805. Functional measures using blood-oxygen level dependent (BOLD) functional magnetic resonance imaging (fMRI) and structural volume estimates using MRI of brain regions responsible for motivation, memory, learning that include by way of example the cingulate cortex, hippocampus, and entorhinal cortex, are further overlaid on the time-series of 805.

The attribution report in 807 computes the contribution of behavioral activity inferred from the recordings in 409-415 to changes in cognitive function evaluated in 725-729. In 809, the attribution report is used to set optimal target levels for mobility, physical, social, learning, diet, and physiology to restore and improve cognitive function. To help the user achieve those targets, information is provided in 811 that directs the user to relevant groups, forums, and educational material. The cycle then repeats itself.

After a target interval of one or two weeks has passed, new behavioral trend reports are published in 803 and compared against the set targets, new values are computed for cognitive function and plotted in 805 to determine whether the target cognitive function was attained, new attributions are evaluated in 807 to explain observed changes in cognitive function, and new targets are set in 809.

Figure 8B:
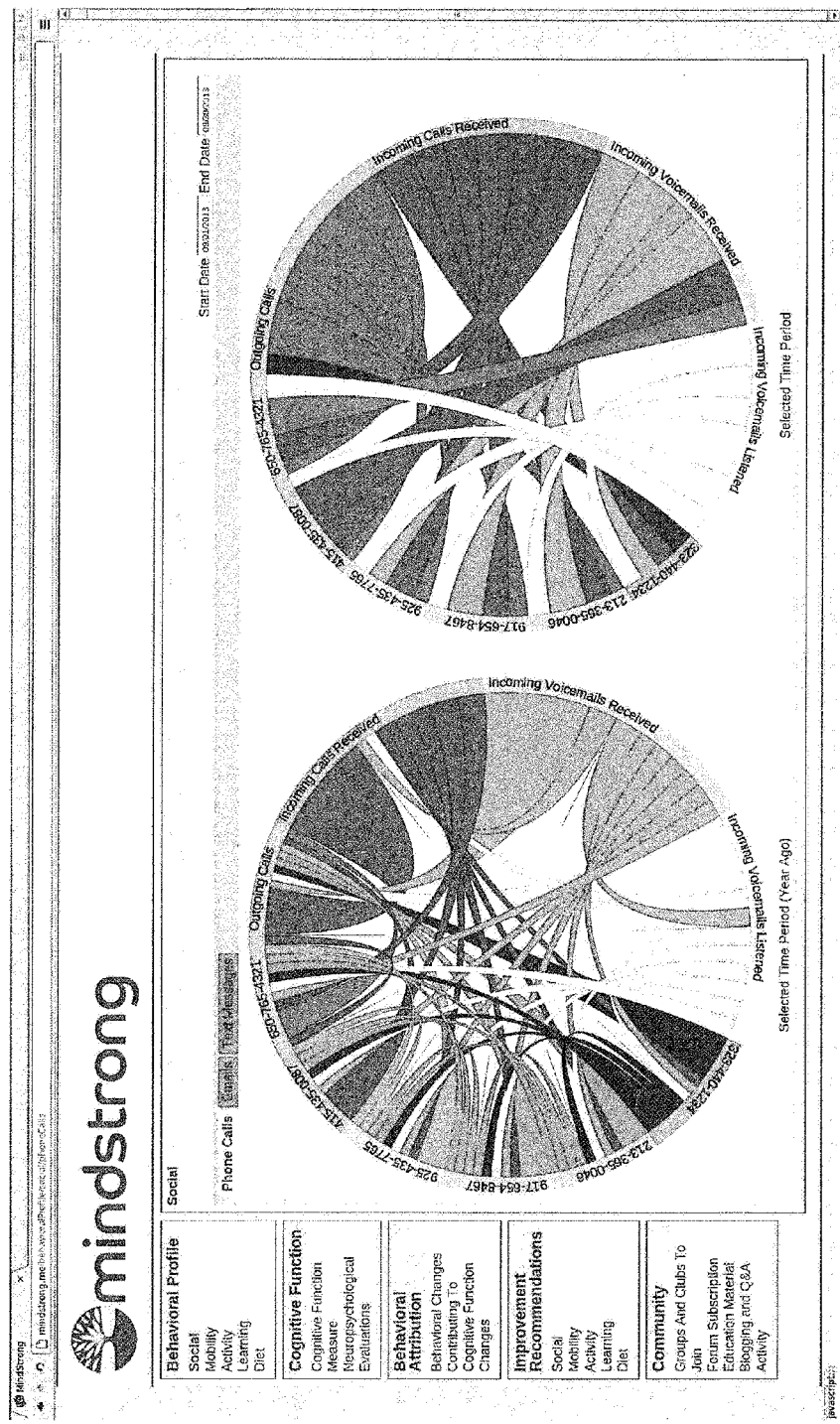
Figure 8C:
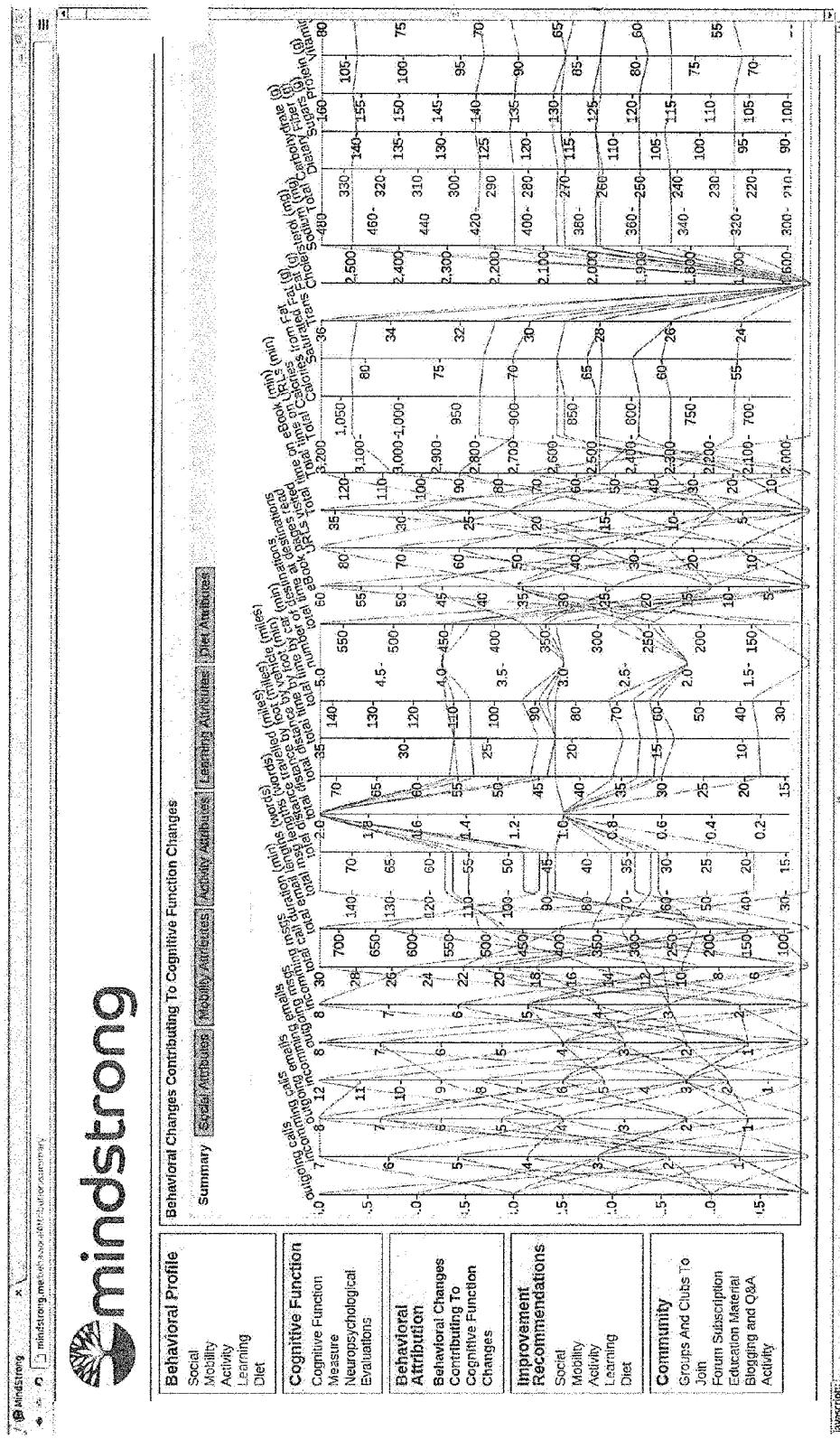

FIG. 8(*b*) illustrates an example behavioral profile report configured in accordance with the present invention and is not intended to limit scope as one of ordinary skill would understand on review of this application that other configurations could be utilized without departing from the scope of the claimed invention. Referring to FIG. 8(*b*), the example profile report for social engagement 813 displays on the right, a chord chart with the number of outgoing calls made, incoming calls received, incoming voicemails received, and incoming voice mails listened to for the month of September 2013. On the left, a chord chart displays the same profile for the user but for the month of September one year ago in 2012. This chord chart reveals greater social engagement as measured by calls made and received in September a year ago than for September in the present year.

The view displayed in 813 is set to the Phone Calls tab. Tabbing to the Emails and Text Messages tab would display similar chord charts for the volume of outgoing and incoming emails and text messages made, received, and opened for the selected time period, their length and volume to or from an email address or phone number, and a comparison chord chart for the same time period one year ago.

FIG. 8(*c*) illustrates an example attribution report configured in accordance with the present invention and is not intended to limit scope as one of ordinary skill would understand on review of this application that other configurations could be utilized without departing from the scope of the claimed invention. Referring to FIG. 8(*c*), the example attribution report 815 displays a parallel coordinate chart that highlights the user's behavioral changes that contribute to changes in measured cognitive function. Each trajectory in the parallel coordinate chart represents a daily aggregate of the user's social, mobility, activity, learning, and diet behavior. Marked deviations in these trajectories capture daily deviations in behavior. In 815, the tabs Social Attribution, Mobility Attribution, Activity Attribution, Learning Attribution, and Diet Attribution display the attribution of social, mobility, activity, learning, and diet behavioral changes to changes in the user's cognitive function.

FIG. 9(*a*)-(*c*) illustrate an embodiment of the key stroke, gesture, and GPS log data encoded unobtrusively by the in vivo monitoring module configured in accordance with the present invention and is not intended to limit scope as one of ordinary skill would understand on review of this application that other key stroke, gesture, and GPS log data can be encoded unobtrusively without departing from the scope of the claimed invention. Referring to FIG. 9(*a*), 901 is key log data captured by the in vivo monitoring module and transmitted to a cloud computer. The session_id column defines the user's session that is unique to the application he/she used when keying "hello world". To determine which application was used we review the app log data to find the application that was launched at the time the key log entries were made. In this particular instance, the entry was made into the text messaging application. In 901, a key_type of value one represents an alphanumeric key and two represents a control key. The ASCII key code is captured in the third column of 901 and the key description is captured in the fourth column. The fifth, sixth, and seventh columns of 901 capture the key press time, the key release time and the key press duration time computed as the difference between the key press and key release times. In addition, the key latency time, not shown, can be computed as the difference between the key_press_time of the key and the key_release_time of the prior key.

Referring to FIG. 9(*b*), 903 is gesture log data captured by the in vivo monitoring module and transmitted to a cloud computer. Each gesture generates a row of data in 903. The application that receives the gesture is captured in the first column, app_pkg_name. An application can have multiple views, and the second column in 903, view_name_in_pkg, captures the particular view that receives the gesture. In 903, gestures were applied to the email inbox ListView. The third column, scroll_unit, has value one if the scroll units are items and value two if the scroll units are in pixels. In 903, the scroll unit for the email inbox ListView is items. The item_count column shows thirty items in 903 meaning that the inbox on that mobile device had a total of thirty emails available for scrolling. The next two columns, from_jdx and to_jdx, capture the items in the list of thirty that were visible at the end of the gesture. At the end of the first gesture shown in the first row in 903, emails two through ten were visible and by the end of the last gesture shown in the last row in 903, emails 21 through 29 were visible. The following three columns in 903 are scroll_direction, max_scroll, and scroll_value. These columns are non-zero only when the scroll unit is pixels. The last column in 903 is the date and time the gesture was made.

Referring to FIG. 9(*c*), 905 is GPS log data captured by the in vivo monitoring module and transmitted to a cloud computer. Each row in 905 captures the GPS latitude, longitude, altitude (in meters above sea level), bearing (ranging from 0 to 360 degrees with North at 0 degrees), and speed (in meters per second). The date and time at which the GPS coordinates and data was captured is in the timestamp column in 905. The accuracy column represents the radius, in meters, of the 68% confidence interval for the latitude and longitude location. In 905, the data reveals that the user travelled South on Interstate 280 from San Francisco and took the El Monte exit off Interstate 280. The user travelled at speeds ranging from 63.9 mph to 77.2 mph until the user reached the Page Mill exit on Interstate 280 where the user's speed decreased to 12.3 mph. In 905, GPS measurements are taken every five-minute.

An individual on any given day of the week uses his or her mobile device regularly as a common way of communicating to others, as a form of entertainment and as a means of retrieving and storing information. Therefore, the technology as disclosed and claimed herein does not require supervision over the individual users and in order to obtain meaningful information that is useful for measuring cognitive function and the individual does not have to change his/her lifestyle for the information to be gathered. For example, an individual may select an application on a mobile computer to launch the application by tapping on an icon displayed as part of the user interface where the user taps the touch-screen to open an application. The individual can launch an application such as a weather application to check the weather forecast, launch an email application to check the email, scroll through emails and read and respond to some emails by keying in text with some typing errors and some misspellings. The user may get up for an early morning walk or run or bike ride and a combination of information may be captured by the global position function of the device as well as information or data from the gyroscopic motion sensor of the device indicative of the user exercising. When walking the user may trip or stumble quite often or their motion may not be fluid, which may be capture by the accelerometer and gyroscopic motion sensor as a sudden and violent movement. Also the user may actually trip and fall. The user may go for a drive over what appears to be a familiar route, but the GPS function captures what appears to be a series of incorrect turns. This may be indicative of a problem, although it may also be captured that the individual is also placing a call, on a call, or sending a text at the same time that the false or incorrect turn was made. The user can open a navigation application and enter a location search query and can use touch-screen gestures to scroll around on map within an application and select items on the map for additional feature information. When scrolling through the map, the individual can touch and swipe the map to follow highlighted directions or to search for a point of interest. Touches that dwell too long or swipes that are too short may result in an undesired response from the mobile computer. During the day, the individual may be traveling to and fro solo, but may need to reach out to their spouse, or son or daughter to coordinate a pick-up or meeting. The user can type text messages to selectively reach out. The individual may continue a text dialogue for a period of time. During the text dialogue the individual may have to back space several times to correct a typing error. The individual may want to meet with their spouse for dinner, but they do not know exactly were the restaurant of choice is located. The user can use the voice command feature to request directions and the GPS can be tracking the user's location, the user can request other content by keying in on a keyboard presented by the application or use voice commands to do the same, read and scroll through content, and the user can make calls or listen to messages. The user's activity is recorded on the device's persistent storage. The user makes or receives calls, email messages, and text messages. There can also be several days in a row where the user is carrying his/her mobile device, but out of the ordinary, the user may not place any call or send any text messages, browse their favorite social media application or visit their favorite website.

The date and time of each of the above activities, the activity duration, and the sender and recipient phone number or email address can be recorded in the device's persistent storage. The frequency of each event is recorded and the various qualitative characteristics of each event are also recorded. The user carries the mobile device with them while driving, using public transportation, walking, biking or running. While engaging in these activities, the mobile device's global positioning system (GPS) records the user's longitude and latitude coordinates. Similarly, during those activities the device's acceleration and gyroscopic motion along a 3-coordinate system is recorded. The type of locations that the individual traveled can be determined and the characteristic of the motion of the user can also be evaluated for fluidity or erratic motion. This information is recorded in the device's persistent storage. The user browses URLs on an internet browser application resident on the mobile device, or reads an e-book on an e-book reader resident on the mobile device. The URLs browsed and the pages of the e-book read, the start time and end time between URLs and pages are recorded by the system and method of this invention and persisted in the device's persistent storage.

Note that all gesture activity, typing activity, and voice command activity during the use of applications is captured separately in and recorded with the time and application in which that activity took place. In this way, the system tracks gestures used during browsing, paging and scrolling, for example. Lastly, a bar code scanning application resident on the mobile device enables the user to scan grocery purchases, and meals and beverages purchased when the latter have bar codes. The bar code scanning application has access to a database of nutritional facts. If the nutritional fact for the scanned bar code is not in the database, then the application instructs the user to photograph the nutritional fact label of the item. The bar code information and any photographs are persisted in the device's persistent storage.

The data captured in the device's persistent storage can be transmitted to cloud computers. Transmission can use a secure channel and can use hypertext transfer protocol secure (HTTPS) to securely transfer the data. The cloud computers can analyze the recorded data against historical recordings and against recordings averaged over other users demographically matched to the existing user. The output of the analysis is an evaluation of cognitive function and the attribution to changes in behavioral activities inferred from the activities recorded in including social engagement, physical activity, learning activity, and diet. The user logs into his or her personal password protected online account to view the results of the analysis together with suggestions for improvement.

Various recordings of data representative of the quantity and quality of interactions and occurrences of events using the mobile computing device can be made. The data can be encoded with representative tags.

A description of the type of encoded data with representative log semantics when an application is launched on the mobile device is as follows:

| App Log | Description |
| --- | --- |
| app_pkg_name | Application launched |
| app_start_time | Start date and time of use |
| app_end_time | End date and time of use |

A description of the type of encoded data with representative log semantics following incoming, outgoing and missed calls on the mobile device is as follows:

| Call Log | Description |
| --- | --- |
| call_type | Values (1, 2, 3) meaning (incoming, outgoing, missed) |
| phone_number | Phone number of call |
| call_start_time | Start date and time of call |
| call_end_time | End date and time of call |
| audio_recording_file | File name of recorded call and null if not recorded |

A description of the type of encoded data with representative log semantics following gestures made on the touch-screen of the mobile device during use of an application is as follows:

| Gesture Log | Description |
| --- | --- |
| app_pkg_name | Application in use |
| view_name_in_pkg | Package within application (eg. Contacts or missed calls, in phone application) |
| scroll_unit | Values (1, 2) meaning (items, pixels) |

-continued

| Gesture Log | Description |
| --- | --- |
| item_count | Number of scrollable items |
| from_idx | Index of first item visible when scrolling |
| to_idx | Index of last item visible when scrolling |
| scroll_direction | Values (1, 2) meaning scroll in (X, Y) direction |
| max_scroll | Max_scroll x dir (or y dir): gives the max scroll offset of the source left edge (or top edge) in pixels |
| scroll_value | Scroll_value X dir (or Y dir): gives the scroll offset of the source left edge (or top edge) in pixels |
| timestamp | Date and time |

A description of the type of encoded GPS data with representative log semantics on the mobile device is as follows:

| GPS Log | Description |
| --- | --- |
| latitude | Latitude of current location |
| longitude | Longitude of current location |
| altitude | Altitude of current location |
| bearing | Horizontal direction of travel in degrees (0.0, 360.0] |
| speed | Travel speed in meters per second |
| accuracy | Radius in meters of 68% confidence circle |
| timestamp | Date and time |

A description of the type of encoded data with representative log semantics when the keyboard is used on the mobile device is as follows:

| Key Log | Description |
| --- | --- |
| session_id | Identifies each session |
| key_type | Values (1, 2) meaning (alphanumeric, control key) |
| key_code | Ascii code of pressed key |
| key_desc | Either the alphanumeric value or a control descriptor |
| key_press_time | Date and time in milliseconds when key is pressed |
| key_release_time | Date and time in milliseconds when key is released |
| key_press_duration | Duration of key press in milliseconds |

A description of the type of encoded sensor data with representative log semantics on the mobile device is as follows:

| Sensor Log | Description |
| --- | --- |
| sensor_type | Values (1, 2) meaning (accelerometer, gyroscope) |
| value_0 | Value of first coordinate measurement |
| value_1 | Value of second coordinate measurement |
| value_2 | Value of third coordinate measurement |
| timestamp | Date and time of coordinate measurements |

A description of the type of encoded data with representative log semantics when text messages are sent or received on the mobile device is as follows:

| SMS Log | Description |
| --- | --- |
| sms_type | Values (1, 2) meaning (Incoming, Outgoing) |
| phone_number | Phone number of message |
| message | Message text |
| timestamp | Date and time of message |

A description of the type of encoded data with representative log semantics when URLs are browsed on the mobile device is as follows:

| URL Log | Description |
| --- | --- |
| URL | URL viewed |
| timestamp | Start date and time of URL view |

In one implementation of the method and system, in order to establish a baseline of data, supervised benchmark testing can be conducted on an initial test group of individuals where these individual take a neuropsychological benchmark test for cognitive function and the data is stored. Each of the same individuals who are tested can be provided with mobile devices having the computer program for performing the system and method. Data for each individual can be recorded as outlined herein and the data from the mobile device usage can be correlated to the benchmark testing results and cognitive function. Cognitive function levels and bands can also be determined from the result. Once certain baselines have been established and correlations are made between cognitive function and mobile device usage, all subsequent mobile device usage by individuals can be utilized to improve the system and method as learning occurs. The learning from the subsequent mobile device usage can be considered unsupervised learning.

The cognitive function module accesses the recordings made by the in vivo monitoring module and transmitted to the cloud computers. Patterns in a user's interactions with a mobile device captured are analyzed for changes in cognitive function. The above described activity for an individual and his interface with a mobile computing device can be captured and utilize. Changes in applications opened and closed by a user, frequency and latencies between opening and closing, and their diurnal and weekly variations are inputs to the feature extraction, learning, and computation of cognitive function. Changes in a user's gestures on a touchscreen such as type of gesture, gesture durations, including false positive gestures of excessive scrolling during search and excessive paging during browsing, are additional inputs to the feature extraction, learning, and computation.

Similarly, when the above described individual makes character inputs, recurring spelling mistakes, omissions, excessive backspace corrections, irregular latency variances in common words, length of messages, and message coherence can all be inputs into the feature extraction, learning, and computation of cognitive function. Signal processing of speech and voice provides additional input to the computation including emerging irregularities in phones and phoneme latencies, and narrowing or shifting of the voice frequency spectrum. The time of day and day of week are captured in the recordings of and used by the cognitive function computation to adjust, or explain variances that can be attributed to individual fatigue and other factors that have short-term effects on cognitive function.

Further, to correct for motion artifact such as from driving or walking, GPS, gyroscope and accelerometer recordings made are used as additional inputs in the feature extraction, learning and computation of cognitive function. To correct for physiologic effects such as anxiety, general malaise, illness, the physiologic measurements of heart-rate, blood pressure, blood glucose, blood oxymetry, and body temperature when available and recorded are used as further inputs to the evaluation of cognitive function. Behavioral activities recorded on the mobile device are analyzed to explain changes in the cognitive function that is computed using inputs. A user's incoming and outgoing email, phone calls, and text messages, their frequencies and length are used as a proxy for the user's level of social engagement. A user's daily travel, the inferred mode of travel including vehicle, bicycle, foot or other, the user's sleep and rest patterns inferred by mobile device "quiet" times, are used to infer physical activity. When this data is available and when correlated with physical activity data such as rapid heart rates from anxiety or illness are distinguished from exercise induced changes, improving the inference of physical activity and quantifying the intensity of that activity. Analysis of patterns in groceries purchased, food and drinks consumed provides a proxy to nutritional intake is also made.

The various implementations and examples shown above illustrate a method and system for assessing cognitive function using a mobile computing device. A user of the present method and system may choose any of the above implementations, or an equivalent thereof, depending upon the desired application. In this regard, it is recognized that various forms of the subject method and system could be utilized without departing from the spirit and scope of the present implementation.

As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present implementation. Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a smart phone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The example computer system and client computers include a processor (e.g., a central processing unit (CPU) a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system and client computing devices also include an alphanumeric input device (e.g., a keyboard or touch-screen), a cursor control device (e.g., a mouse or gestures on a touch-screen), a drive unit, a signal generation device (e.g., a speaker and microphone) and a network interface device.

The drive unit includes a computer-readable medium on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

I claim:

1. A computer implemented method to quantify the effect of social interaction, mobility, physiology, cognitive stimulation, and diet on a person's brain health, said method comprising the steps of:
   a. recording at a mobile computing device an in vivo input associated with a measurement of one of social interaction, mobility, physiology, cognitive stimulation, and diet;
   b. recording interaction inputs associated with one or more interactions of the person with said mobile computing device;
   c. executing a learning function mapping to compute a brain health measure based on said person's interaction inputs, wherein said brain health measure is one of a neuropsychological benchmark test;
   d. performing the learning function mapping from said recording associated with the in vivo input to said computed brain health measure; and
   e. outputting an attribution to said brain health measure that is explained by said in vivo input.

2. The method of claim 1, wherein the one or more interactions includes at least one of: applications opened, inputs typed, gesture patterns used on a touch screen, body motions, and voice input.

3. The method of claim 1, wherein the mobile computing device is one of: a smart phone, a tablet computer, and a wearable mobile computing device.

4. The computer implemented method of claim 1, wherein the social interaction measurement is one of length, duration, frequency, volume, sentiment, and mood associated with an incoming call, an outgoing call, a text, and an email message.

5. The computer implemented method of claim 1, wherein the social interaction measurement is from one of an email, text, phone, or other communication application on said mobile computing device.

6. The computer implemented method of claim 1, wherein the mobility measurement is one of intensity, duration, and frequency of locomotor activity.

7. The computer implemented method of claim 1, wherein the mobility measurement is from one of an accelerometer application and a gyroscope application on said mobile computing device.

8. The computer implemented method of claim 1, wherein the physiology measurement is one of a heart rate, a blood pressure, a blood oxymetry, a blood glucose, a body temperature, a body fat, a body weight, a sleep duration and quality, and an electroencephalogram.

9. The computer implemented method of claim 1, wherein the cognitive stimulation measurement is one of URLs visited, books and articles read online, and games played on said mobile computing device.

10. The computer implemented method of claim 1, wherein the cognitive stimulation measurement is one of a setting of, or a recording from, a brain stimulation device.

11. The computer implemented method of claim 1, wherein the diet measurement is one of a caloric intake, a nutritional value, a food type, alcohol, caffeine, a drug, a medication, and a vitamin consumed.

12. A computer-readable medium comprising instructions that when executed by a processor running on a computing device perform a method to quantify the effect of social interaction, mobility, physiology, cognitive stimulation, and diet on a person's brain health, said method comprising the steps of:
  a. recording at a mobile computing device an in vivo input associated with a measurement of one of social interaction, mobility, physiology, cognitive stimulation, and diet;
  b. recording interaction inputs associated with one or more interactions of the person with said mobile computing device;
  c. executing a learning function mapping to compute a brain health measure based on said person's interaction inputs, wherein said brain health measure is one of a neuropsychological benchmark test;
  d. performing the learning function mapping from said recording associated with the in vivo input to said computed brain health measure; and
  e. outputting an attribution to said brain health measure that is explained by said in vivo input.

13. The computer-readable medium of claim 12, wherein the one or more interactions includes at least one of: applications opened, inputs typed, gesture patterns used on a touch screen, body motions, and voice input.

14. The computer-readable medium of claim 12, wherein the mobile computing device is one of: a smart phone, a tablet computer, and a wearable mobile computing device.

15. A computer-implemented system for assessing the effect of social interaction, mobility, physiology, cognitive stimulation, and diet on a person's brain health, the system comprising:
  a. a mobile computing device that:
    records an in vivo input associated with a measurement of one of social interaction, mobility, physiology, cognitive stimulation, and diet; and
    records interaction inputs associated with one or more interactions of the person with said mobile computing device; and
  b. a computing system comprising a processor, said computing system:
    computing a brain health measure by performing a learning function mapping from said interaction inputs to said brain health measure, wherein said brain health measure is a neuropsychological benchmark test;
    performing the learning function mapping from said in vivo input to said computed brain health measure; and
    outputting an attribution to said brain health measure that is explained by said in vivo input.

16. The system of claim 15, wherein the one or more interactions includes at least one of: applications opened, inputs typed, gesture patterns used on a touch screen, body motions, and voice input.

17. The system of claim 15, wherein the mobile computing device is one of: a smart phone, a tablet computer, and a wearable mobile computing device.

* * * * *